United States Patent [19]

Smeets

[11] 3,997,596
[45] Dec. 14, 1976

[54] UNSATURATED CARBOXYLIC SALT MATERIALS AND DERIVATIVES THEREOF

[75] Inventor: Fred Smeets, Tienen, Belgium

[73] Assignee: Citrex S.A., Saint-Gilles-lex-Brussels, Belgium

[22] Filed: Nov. 18, 1975

[21] Appl. No.: 633,039

Related U.S. Application Data

[60] Continuation of Ser. No. 877,588, Nov. 24, 1969, abandoned, which is a division of Ser. No. 563,816, July 8, 1966, Pat. No. 3,586,715.

[30] Foreign Application Priority Data

July 19, 1965 United Kingdom ............ 30640/65

[52] U.S. Cl. .................... 260/513 B; 260/456 R; 252/99; 252/550; 252/551; 252/553
[51] Int. Cl.$^2$ ....................... C07C 143/12
[58] Field of Search ................. 260/513 B

[56] References Cited

UNITED STATES PATENTS 2,602,057  7/1952  Groote .................... 260/513 R

*Primary Examiner*—James O. Thomas, Jr.
*Assistant Examiner*—Nicky Chan
*Attorney, Agent, or Firm*—Cushman, Darby & Cushman

[57] ABSTRACT

A novel sulphonated salt is prepared by pyrolyzing an alkaline-earth metal salt of citric acid until an increase in titratable alkalinity is reached, whereby a novel unsaturated organic salt material is obtained. That salt material is dissolved or suspended and thereafter contacted with a bisulphite ion under acid conditions for producing the sulphonated salt. The corresponding acid of the sulphonated salt may be obtained by hydrolyzing the salt either prior to or subsequent to the sulphonation step.

11 Claims, 1 Drawing Figure

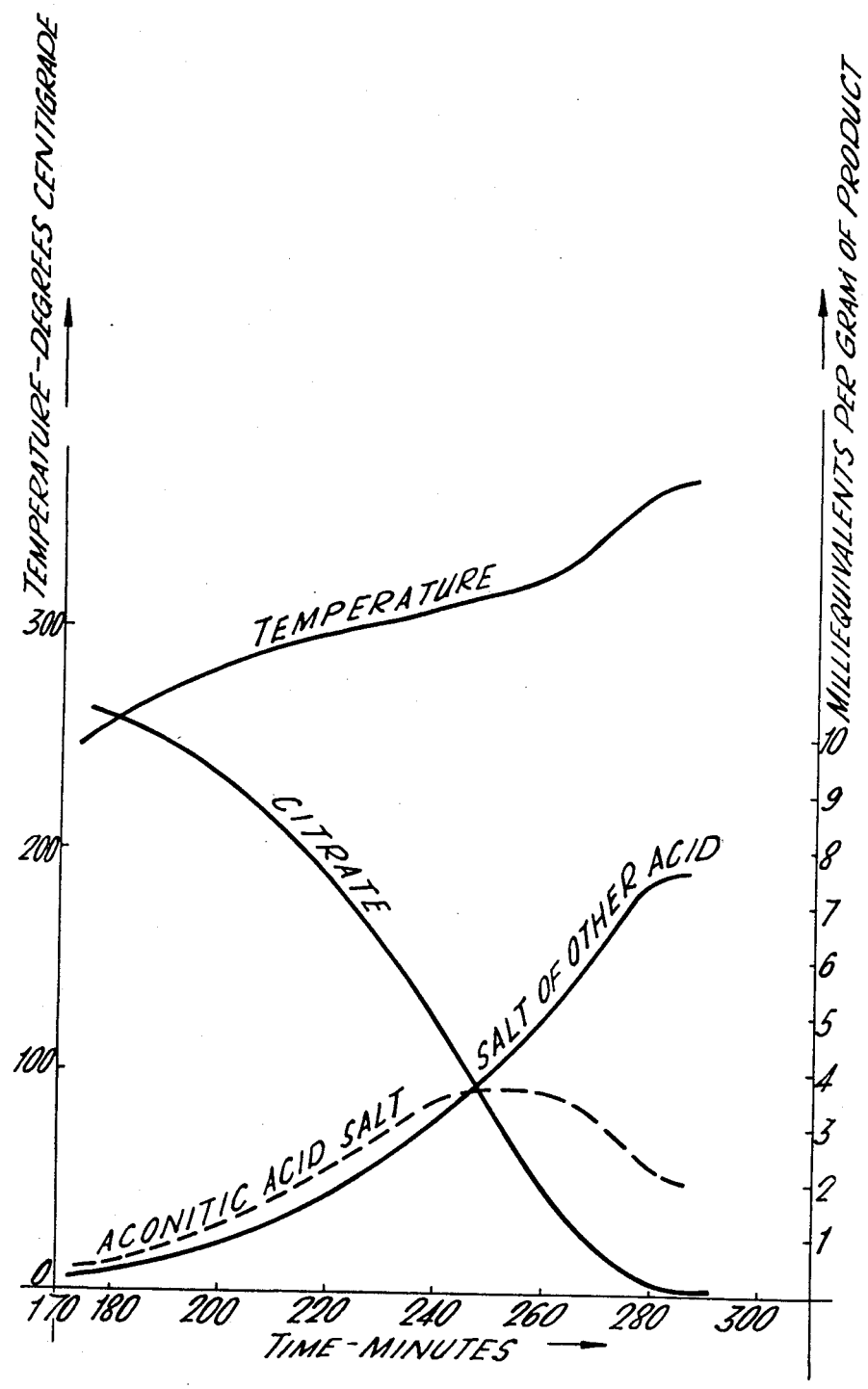

UNSATURATED CARBOXYLIC SALT MATERIALS AND DERIVATIVES THEREOF

This is a continuation of application Ser. No. 877,588, filed Nov. 24, 1969, now abandoned, which is, in turn, a divisional of application Ser. No. 563,816, filed July 8, 1966, now U.S. Pat. No. 3,586,715.

This invention relates to unsaturated organic salt materials obtainable from salts of citric acid, and more particularly relates to a method of preparing unsaturated organic salt material by the controlled pyrolysis of an alkaline-earth salt of citric acid. The invention also relates to acid-, sulpho-, ester- and especially sulphoester, derivatives of the said materials, and to condensates including polycondensates. The invention also relates to surface-active materials, including dispersants, detergents, wetting agents, degreasing agents, emulsifying agents, anti-foaming agents, hydrocarbon oil compositions, soluble calcium salts, plastics and plasticizers, obtainable from the said salt materials. The surface-active materials are characterized in being biodegradable.

It has now been discovered that entirely new unsaturated organic salt materials may be obtained if alkaline-earth salts of citric acid are heated for a period of time until an increase in titratable alkalinity is obtained, the salt materials being essentially different from, although they may contain, aconitric acids.

The preferred alkaline-earth salt of citric acid used in the process of the invention is tri-calcium citrate, preferably obtained from fermentation of molasses in the manufacture of citric acid. Other alkaline-earth salts, including barium and magnesium citrates, may be used if desired.

To achieve an acceptable rate of conversion, the citric acid salt is preferably heated to a temperature not less than 230° C, particularly to a temperature within the range of 250° to 400° C, more particularly in the range from 300° to 375° C.

A characterizing feature of the process of the invention is the formation of a titratable alkalinity in the reaction mixture in the course of the reaction, denoting the formation of the new unsaturated organic acid salt material. The onset of the titratable alkalinity may be determined by subjecting the citric acid salt to gradually increasing temperatures, and titrating the alkalinity present in the reaction mixture in consecutive samples taken therefrom. The first sample containing an amount of titrable alkalinity which is higher than that what might occasionally be present as impurity in the starting material and which is thus detectable in the unreacted material, indicates the combination of temperature and time at which the formation of the new salt material is started. If tricalcium citrate is used as starting material, it has been found that the formation of this alkalinity is due to the formation of calcium carbonate, and the course of the reaction is also characterized by the evolution of carbon dioxide when the reaction is carried out under atmospheric pressure. It does not appear, however, that the $CO_2$ has its origin in the calcium carbonate thus formed.

Another characteristic of the process of the invention is the decrease, in the course of the reaction, of the number of carboxylic acid salt groups present in the reaction mixture, and it has been found that the formation of the new acid material is accompanied by a decrease in the ratio of alkaline earth metal bound in organic salt form, to the total amount of alkaline earth metal present in the reaction mixture, i.e. in both organic and inorganic salt form.

A still further characteristic of the process of the invention is that when, in the course of the reaction, consecutive samples of the reaction mixture are treated with a strong acid in order to hydrolyse all the organic alkaline earth metal salts present, the ratio of carboxylic acid groups stemming from aconitic acid present in the reaction mixture to all the carboxylic acid groups present, decreases after an initial increase to a maximum starting from zero, whereas the ratio of carboxylic acid groups stemming from citric acid to all the carboxylic acid groups present constantly decreases from 1 to nearly zero.

Taking into account the above characteristics, it may be assumed that in the course of the process of the invention, a rearrangement occurs within the citric acid salt molecule, whereby carboxylic acid groups are reacting together, resulting in the formation of inorganic metal compounds, and as well as the formation of aconitic acid salts, in the formation of other unsaturated organic salts to form the new acid salt materials of the invention, the said other organic salts being derived from unsaturated and as yet unidentified organic acid which apparently contain more than three carboxylic acid groups per molecule.

The pyrolysis is preferably continued until the concentration of citrate starting material in the reaction mixture is five percent by weight or less, particularly one percent or less. The resulting reaction mixture contains, besides the unidentified unsaturated organic salts, a mixture of inorganic alkaline earth compounds giving rise to titratable alkalinity, a proportion of alkaline-earth aconitate, a small amount of original citrate and traces of coloured compounds. The latter can be eliminated, for instance, by means of adsorbing agents such as activated carbon. Thus by the process of the invention the alkaline-earth citrate starting material can be substantially quantitatively transformed into the new unsaturated organic salt materials of the invention.

The pyrolysis reaction can be carried out using well-known techniques for the pyrolysis of compounds, amongst which the following procedures may be mentioned:

a. the citrate is spread out in trays, and heat is applied. A thermoregulator controls the temperature of the reaction mixture, which is increased gradually till the desired degree of pyrolysis is attained;

b. the citrate is heated in a rotating cylinder, in which the temperature may be controlled by means of a recording thermoregulator;

c. the pyrolysis of the citrate is performed in a continuous manner in an inclined rotating cylinder. In this procedure the time the products take for passing through the cylinder as well as the temperature are regulated accurately;

d. the pyrolysis of the citrate is performed by flash-heating using commercially available flash-heating units;

e. the pyrolysis of the citrate is performed by contact with hot inert liquids or gases such as nitrogen, carbon dioxide or superheated steam;

f. the pyrolysis is carried out using a fluidized technique, in which the supporting gas is inert and forms the heating medium.

Any of the above techniques may be carried out under reduced pressure, at atmospheric pressure or at superatmospheric pressure.

The salt materials according to the invention may be transformed into the corresponding acid materials by application of any of the methods known in the art for conversion of carboxylic acid salts into the corresponding acids.

Thus, for instance, when tricalcium citrate is used as starting material, the reaction mixture obtained by the pyrolysis and containing a calcium salt of an unidentified organic acid, calcium aconitate and calcium carbonate, can be treated with sulphuric acid, and the precipitate of calcium sulphate formed separated, for example, by filtration, and the remaining acid solution concentrated, preferably by heating under reduced pressure, if desired until crystallisation occurs. After separating the crystals from the acid solution, e.g. by centrifuging, the aconitic acid can, if desired, be eliminated by fractional crystallisation or by fractionated extraction with organic solvents.

If desired, the separation of one or more acids containing less than four carboxylic groups, or derivatives thereof, may be effected on the acid material obtained by the pyrolysis, or on the corresponding sulpho-acid, ester, or sulpho-ester materials hereinafter described, for instance by fractional crystallisation, distillation or extraction techniques.

The following Examples 1 to 4 are examples of the preparation of salt materials, and the corresponding acid materials, according to the invention.

EXAMPLE 1

25 kg of tricalcium citrate $4H_2O$ were introduced into a rotating cylinder having a volume of 190 liters, a diameter of 55 cm and a length of 80 cm. The cylinder was placed in an electrically heated oven and rotated at a speed of 10 r.p.m. The temperature was gradually raised from 20° to 365° C over a period of time of 6 hours.

During the period of heating, samples of the reaction mixture were from time to time removed, and analyzed to determine a. the amount of tricalcium citrate remaining in the reaction product, by microanalysis b. the amount of aconitic acid salt generated in the reaction mixture, determined by microanalysis c. the amount of other organic salt(s) generated in the reaction product. This was determined by subtracting the amount of citric acid equivalent and aconitic acid equivalent from the total acid equivalent in the reaction product.

The total acid equivalent was determined by adding a known weight of reaction product to an agitated dispersion of a cationic exchanger. Calcium ions taken up by the exchanger liberate an equivalent amount of acid, and evolved $CO_2$ driven off by heating. The milliequivalent of the acid is determined by titration with standard NaOH.

d. The amount of inorganic compound (calcium carbonate) produced in the reaction product, by titration.

The results obtained are shown in Table 1.

TABLE 1

| Time Minutes | Temperature Degrees Centigrade | Ca tricitrate (as acid equivalent) remaining in product | Ca aconitate (as acid equivalent) in product | Other organic Ca Salt (as acid equivalent) in product | Inorganic metal compound |
|---|---|---|---|---|---|
| | | Expressed as milliequivalents per gram of product | | | |
| 177 | 253 | 10.5 | 0.5 | 0.5 | 0.1 |
| 187 | 268 | 10.3 | 0.8 | 0.4 | 0.2 |
| 197 | 279 | 9.3 | 1.0 | 1.1 | 0.3 |
| 207 | 287 | 8.8 | 1.5 | 1.1 | 0.4 |
| 217 | 295 | 7.7 | 2.0 | 1.7 | 0.5 |
| 227 | 301 | 6.6 | 2.6 | 2.2 | 0.8 |
| 237 | 307 | 5.0 | 3.3 | 2.9 | 1.1 |
| 247 | 315 | 3.6 | 3.6 | 3.9 | 1.5 |
| 267 | 335 | 1.1 | 3.4 | 5.9 | 2.6 |
| 273 | 350 | 0.5 | 2.9 | 6.8 | 3.0 |
| 279 | 360 | 0.2 | 2.2 | 7.5 | 3.3 |
| 281 | 365 | 0.1 | 2.3 | 7.4 | 3.5 |
| 286 | 365 | 0.1 | 2.1 | 7.5 | 3.6 |

These results are shown graphically in the accompanying drawing, from which it is to be observed that during the course of the reaction a fall in the amount of citrate present in the reaction mixture was accompanied by an increase in the amount of other organic acid salts. The initial increase in the proportion of aconitic acid salt is also shown, followed by a characteristic decrease in the amount of this product in the reaction mixture at higher temperatures is also shown. It will also be observed that the other organic acid salt is not generated in substantial proportions at temperatures below about 220° C. under the conditions of the preparation.

The proportion of calcium carbonate compound generated during the reaction is not shown in the drawing, but it may readily be deduced from Table 1 that there is an approximate correspondence between the amount of calcium carbonate and the amount of organic acid other than aconitic acid, produced.

Table 2 gives the amounts of the various products in the reaction mixture, expressed as gram percentages.

TABLE 2

| Time minutes | Temperature Degrees Centigrade | Calcium citrate gram percent | Calcium aconitate gram percent | $CaCO_3$ gram percent |
|---|---|---|---|---|
| 177 | 253 | 91.6 | 3.7 | 0.7 |
| 187 | 268 | 89.6 | 5.8 | 1.0 |
| 197 | 279 | 81.0 | 7.8 | 1.4 |
| 207 | 287 | 77.4 | 11.4 | 1.8 |
| 217 | 295 | 68.1 | 15.7 | 2.6 |
| 227 | 301 | 58.0 | 20.2 | 3.9 |
| 237 | 307 | 45.3 | 25.5 | 5.4 |
| 247 | 315 | 32.6 | 28.1 | 7.6 |
| 267 | 335 | 10.4 | 26.1 | 13.1 |
| 273 | 350 | 5.0 | 22.3 | 14.9 |
| 279 | 360 | 1.9 | 17.0 | 16.7 |
| 281 | 365 | 1.2 | 17.4 | 17.5 |
| 286 | 365 | 0.8 | 16.3 | 18.1 |

EXAMPLE 2

10 kg of anhydrous tricalcium citrate were spread on trays mounted on a frame in an oven, in layers about 3 cm deep. The initial temperature of the oven was gradually raised from 250° C to 325° C over a period of one hour, and the pyrolysis continued for 8 hours at 325° C. The reaction mixture obtained contained besides calcium carbonate the calcium salts of different polycarboxylic acids. Analysis of the acid solution obtained by the addition of sulphuric acid to an aqueous dispersion of the reaction mixture and filtering off the formed calcium sulphate, showed that it contains, besides a very small amount of citric acid and a minor amount by weight of aconitic acid, a major amount of another polycarboxylic acid which was different from aconitic acid. From the above, it appears that the reaction mixture obtained by the pyrolysis of the tricalcium citrate contained a substantial amount of the calcium salt of a further polycarboxylic acid composition which was different from calcium aconitate.

EXAMPLE 3

25 kg of tricalcium citrate $4H_2O$ were introduced into a rotating cylinder having a volume of 190 l., a diameter of 55 cm and a length of 80 cm. The cylinder was placed in an electrically heated oven and rotated at a speed of 10 revolutions per minute. The temperature was gradually raised from 20 to 325° C in 4½ hours, and thereafter held for 4 hours at 325° C.

10 kg of the obtained reaction reaction mixture were dispersed in 50 l. of water. Thereafter, 6.8 kg of concentrated sulphuric acid (66° Be) were gradually added over a period of 1 hour. Calcium sulphate thus formed was filtered off, and a solution was obtained containing, besides a minor amount of aconitic acid, a major amount by weight of a further polycarboxylic acid composition. This solution was concentrated by heating under reduced pressure until a total concentration of free organic acid of about 11.000 milliequivalents per litre was reached.

EXAMPLE 4

200 grams of tribarium citrate were introduced into a rotating cylinder having a volume of about 3 liters, a diameter of 12.5 cm and a length of 24 cm. The cylinder was electrically heated and rotated at a speed of 6 cycles per minute, changing its direction after each cycle. A flow stream of nitrogen was passed through the cylinder during the period of heating. The temperature was gradually raised from 20° to 310° C over a period of time of 6½ hours. 158 grams of a yellow powder were obtained, which contained, in addition to barium carbonate, the barium salts of different polycarboxylic acids. A dispersion of the salt material was contacted by a cationic exchanger. Analysis of the acid solutions thus obtained showed that it contained besides a small amount of citric acid, a minor proportion of aconitic acid and a major proportion of other polycarboxylic acids.

The acid materials according to the invention can be used as acidifying agents (e.g. in the food industry) and in the preparation of solutions with high calcium content (e.g. in pharmaceutical industry). The calcium salts contained in the salt material obtained by pyrolysis of calcium citrate, which material is preferably treated to remove calcium carbonate, therein, or by neutralisation of the organic acid material obtained by hydrolysis of the acid material with a calcium base, show a surprising and high solubility in water. A peculiar characteristic of such calcium salt solutions is an inverse solubility effect in which a precipitate forms on heating, which precipitate redissolves on cooling.

The sodium salts obtainable by neutralisation of the organic acid material obtained by hydrolysis of the salt material of the invention, are also very soluble. On concentrating a mixture of the said calcium salts the mixture does not precipitate and it is necessary to evaporate the solution to dryness to obtain a powder. The sodium salts have the useful property of assisting in the solubilisation of calcium salts of low solubility, e.g. calcium sulphate.

The new salt as well as the new acid materials are further useful as starting materials for the preparation of different kinds of condensation products, and are especially useful for the preparation of the corresponding unsaturated ester, sulpho-acid and sulpho-ester materials.

The following Example is provided for the formation of unsaturated ester material, according to the invention.

EXAMPLE 5

45.5 l. of the concentrated acid solution obtained as described in Example 3, were mixed with 61.7 kg of 1-pentanol in a vessel, provided with an agitator. 370 g of concentrated sulphur acid (66° Be) were added as catalyst. The reaction was carried out at a temperature between 60° and 100° C, and at a reduced pressure of 50 to 200 mg Hg. The alcohol/water azeotrope was distilled off and collected in a water separator, and the supernatant alcohol was continuously returned to the reaction vessel. The degree of esterification after 8 hours was 97 %. The remaining acidity was neutralised with sodium hydroxide to a pH of 7.0. After distillation of the remaining alcohol at reduced pressure, a mixture containing, besides a minor part of tripentyl aconitate, a major part of the pentyl ester of the new unsaturated polycarboxylic acid composition.

It has been found that the new salt, acid and ester materials hereinbefore described are readily able to undergo an addition reaction with bisulphite ions to produce sulphonated material. The resulting sulphonic acid group is strongly acidic, and is responsible, in the sulpho-acid material, for about 20% of the total acidity thereof, the remaining acidity being due to the presence of carboxylic acid groups.

In the preparation of the new sulpho-materials, various techniques can be employed. Thus, the addition reaction may be carried out either on the reaction mixture obtained by the pyrolysis of the citrate hereinbefore described, to obtain a mixture of sulphonated salts, or on the hydrolysed reaction mixture, to obtain a mixture of sulphonated acids, or on the esterified acid material to obtain a mixture of sulphonated esters.

It is to be understood that said addition reaction may also be carried out in the acid materials according to the invention which have had the aconitic acid removed, as well as on the corresponding salts obtained by neutralization of the acid material.

The bisulphite ions necessary for carrying out said addition reaction may be provided in a solution containing the organic salt or acid material, either as a bisulphite added as such in the form of one of its water-soluble salts, or the bisulphite ion may be formed in situ. If inorganic salt material e.g. calcium carbonate, has not been removed from the salt material according to the invention, a complete solution of the material may not be obtainable, in which instance a dispersion thereof may be used in the sulphonation reaction.

Known methods for the sulphonation of unsaturated polycarboxylic acids may be used to form the sulpho-materials according to the invention, for instance, by treating such material in neutralised or partially neutralised solution or dispersion with an alkali metal bisulphite, such as sodium bisulphite, or with ammonium bisulphite, or by treating the acid (un-neutralised) solution with an alkali-metal or ammonium sulphite which is transformed in situ into the corresponding bisulphite, for instance as described in British Pat. Specification No. 551,246 and in U.S. Pat. No. 2,315,375. Taking into account, however, the high solubility of calcium salts of the new acid materials of the invention, it has been found that the alkali-salt bisulphites or sulphites can be replaced by calcium bisulphite or calcium sulphite.

According to a preferred embodiment of the invention, the bisulphite ions are provided in situ by injecting sulphur dioxide into a solution containing the salt material, obtained by the pyrolysis of the citrate. Thus, sulphur dioxide may be injected into an aqueous dispersion of the reaction mixture obtained by the pyrolysis of tricalcium citrate, calcium bisulphite being formed in situ. It is preferred to neutralise wholly or partially the inorganic alkaline-earth compound, e.g. calcium carbonate present in the reaction mixture, by the addition of an acid such as sulphuric acid, or an acid or sulpho acid material according to the invention, which may be a recycle new acid or sulpho-acid, before or during the introduction of the sulphur dioxide.

The bisulphite addition reaction is carried out under acid conditions, i.e. at a pH of 7 or less, preferably at a pH of 2 to 5. If the bisulphite is formed in situ by the introduction of sulphur dioxide, the reaction may be carried out at a temperature lower than 100° C in a closed vessel in order to prevent the escape of sulphur dioxide. The use of high pressures is not necessary. After the sulphonation has come to an end, excess sulphur dioxide may be eliminated, and the sulphur dioxide can be recycled into fresh starting solution.

The sulpho acid salt material obtained by the bisulphite addition as hereinbefore described can easily be hydrolysed and transformed into the corresponding sulpho acid material by application of conventional hydrolysis techniques.

When calcium salt materials according to the invention, are used as starting material for the preparation of sulphonated organic acid material, the said materials may be acidified, for instance with a mineral acid, sufficient to cause reaction with inorganic metal carbonate contained therein, and $SO_2$ injected into the solution to form sulphonated organic salt material, the solution then being further acidified, whereby the sulphonated salt solution is hydrolysed to sulphonated acid material. Preferably the product solution is recycled to the initial solution or dispersion before or during the injection of $SO_2$.

The sulpho-acid material thus obtained can be prepared as a highly concentrated solution. The said solution can be used as a catalyst for condensation (e.g. esterification) reactions, or as a pickling agent for metals. Calcium salts of the sulpho-acids are also characterised in having a substantial degree of solubility.

Embodiments of the formation of sulpho-acid materials according to the invention, are provided by the following Examples 6 to 8.

EXAMPLE 6

320 g of solid $Na_2SO_3$ 7 $H_2O$ were added to 1.6 l. of a solution with a total concentration of free organic acid of about 2.500 milliequivalents per liter, and obtained by dilution of the concentrated acid solution prepared as described in Example 3. The pH of the resulting solution was about 3.5. The solution was heated at 80° to 90° C for 12 hours under a pressure of 2 kg/cm2, to obtain substantially completely sulphonated products.

EXAMPLE 7

10 kg of the reaction mixture, obtained by the pyrolysis of tricalcium citrate as described in Example 3, were dispersed in 50 liters of water. Thereafter, 3 kg of sulphur dioxide were gradually introduced over a period of 2 hours at 75° C, under agitation. The addition reaction of the calcium bisulphite thus formed in situ was continued by heating for 18 more hours, at a maximum pressure of 2 kg/cm2, in an autoclave provided with an agitator.

Excess of sulphur dioxide was removed by heating and recovered, whilst 6.8 kg of sulphuric acid (66° Be) were gradually added. After filtering off he calcium sulphate formed, a solution was obtained, containing, besides a minor amount of sulphonated aconitic acid, a major amount of a new sulpho-carboxylic acid composition. This solution was concentrated by heating under reduced pressure until a total concentration of free organic acid of about 10.000 milliequivalents per litre was reached.

EXAMPLE 8

98.1 kg of the reaction mixture, obtained by pyrolysis of tricalcium citrate as described in Example 3, were dispersed in 300 liters of a solution with a total concentration of free acid of about 2.000 milliequivalents per litre, and obtained by dilution of the concentrated acid solution prepared as described in Example 7. Thereafter 25 kg of sulphur dioxide were gradually introduced with agitation over a period of 8 hours at a temperature between 55° and 70° C. In order to obtain a nearly complete sulphonation reaction, heating was continued for 16 more hours at a pressure of 2 kg/cm2.

Excess of sulphur dioxide was removed by heating whilst gradually adding concentrated sulphuric acid and recovered. After filtering off the calcium sulphate formed, a solution was obtained containing, besides a minor amount of sulphonated aconitic acid, a major amount of a new sulpho-carboxylic acid composition. This solution was concentrated by heating under reduced pressure.

The new acid and sulpho-acid materials are particularly useful starting materials for the preparation of different kinds of condensation products, particularly for the preparation of ion-exchange materials, surface active materials, including wetting agents, detergents and dispersants for polar and non-polar systems, e.g. aqueous, organic-polar and hydrocarbon oil (including fuel or lubricating oil) systems, textile oils, degreasing agents for industrial or domestic use, and anti-foaming agents, which surface-active agents are completely or substantially biodegradable.

Surface-active agents according to the invention obtained from the sulphonated materials hereinbefore described are characterised in that they are the sulphonated acid salt ester derivatives of the unsaturated organic salt materials obtained by the process hereinbefore described. The specific properties of the surface-active agents are a function of the metal radical of the sulphonic acid salt, and also a function of the degree of esterification and the chain-length and distribution of the alcohol residues used in the esterification process.

One of the advantages of surface-active agents prepared according to the invention is that they possess the properties of both soaps (i.e. salts of fatty acids) and detergents (e.g. of sulphate or sulphonate of fatty alcohols), and possess advantages over both. Thus while displaying the cleansing power of soaps, they have a low sensitivity to water-hardness, and are equally effective in alkaline and neutral media, and have a particularly low value for critical micelle concentration (C.M.C.). They have good suspending properties, including the prevention of precipitate of calcium or magnesium salts from hard water, and are effective in reducing the surface tension of aqueous media in very low concentrations of a few tenths of one part per million, while useful lowering of surface tensions to about 35 dynes per cm. is obtainable in concentrations of from 1 to 10 parts per million.

The esterification process may be carried out with for example one or more $C_1$–$C_{22}$ monohydric alcohols, or with polyhydric alcohols whereby polycondensates are obtained. Specific examples of polyhydric alcohols which may be used include glycerol, ethylene glycol, diethylene glycol, triethylene glycol and propylene glycol, and sugar alcohols, such as sorbitol and sucrose. A mixture of mono- and polyhydric alcohols may be used.

The esterification may be carried out under conditions such as to provide only partly esterified reaction products. During esterification the water formed in the course of the esterification process may be removed by distillation of the azeotropic mixture of water and the lower alcohol. This procedure is followed when reacting only lower alcohols or a mixture of lower and higher boiling alcohol, the lower alcohol acting also as a solvent. Further it is possible to react the acid materials first with the lower alcohol until completion and then add the higher alcohol or a poly alcohol, which by means of a transesterification reaction replaces the lower alcohol. Usually the distillate is collected in a water separator and the supernatant alcoholic layer returned to the reaction mixture.

After the desired degree of esterification has been reached, the remaining acidity, if any, can be neutralised by the addition of a suitable base and the remaining alcohol distilled off, preferably under reduced pressure. Suitable neutralising agents are sodium hydroxide, or bases of other alkali metal bases such as potassium or lithium, alkaline-earth metal bases, such as for example calcium, magnesium and zinc, or trivalent metal bases such as aluminum oxide or hydroxide. It is also possible to neutralise the acidity by means of ammonia, or organic bases containing basic amino groups e.g. lower and higher amines, and the amino alcohols such as mono-, di- and tri-ethanolamine.

In the process in which the esterification process precedes the bisulphite reaction, a concentrated solution of a water soluble bisulphite is gradually added to the ester material with continuous stirring. A low molecular weight alcohol, such as ethyl alcohol, can be added in order to allow the reaction to proceed homogeneously. The reaction is preferably carried out in a closed vessel in order to facilitate the addition reaction of the bisulphite. The reaction time is dependent upon the speed of which the bisulphite is added to the reaction mixture and upon the reaction temperature, which usually is about 100° C. If a low molecular alcohol was added in the course of the reaction it is distilled off after the sulphonation has been finished.

In the process in which the bisulphite addition reaction precedes the esterification reaction, which method is the preferred method, the sulpho-acid material is subject to esterification. Any of the known esterification techniques applied e.g. the methods described in the British Pat. Specification No. 511,246 and the U.S. Pat. No. 2,135,375, but in most instances the techniques of distilling an azeotropic water mixture is the preferred one. Usually no catalyst is needed, because the strongly acidic sulphonic acid group present in the sulpho-acid material will in most instances sufficiently catalyse the reaction, so that no further catalyst is needed. If in some instances, the reaction velocity is too low, it may be advantageous to convert the new sulpho-acid material into a still more reactive form, such as the chloride, prior to esterification.

At the end of the esterification reaction, neutralization of the remaining acidity may be carried out as hereinbefore described.

In general, all types of surfactive compositions according to the invention can be obtained from a single alcohol, useful results may be obtained when a mixture of alcohols is used for esterification. When comparing a homologous series of surfactants according to the invention, it is found that there is a gradual transition from primarily wetting agents to anti-foam agents. By homologous series in this context, is meant a series obtained by using different long chain alcohols, such as for example, octyl, decyl, lauryl, myristyl, cetyl, stearyl and oleyl alcohol, to esterify a fixed percentage of carboxyl groups, and a single lower alcohol such as for example ethyl, propyl, butyl, amyl and hexyl alcohols, including branched or unbranched, primary, secondary or tertiary alcohols, to esterify the remaining carboxyl groups. Using this technique it is possible to find an optimum sulpho-ester according to the invention, for each type of surfactivity, combined with the highest efficiency for the lowest cost.

When starting from one or more $C_1$–$C_8$ monohydric aliphatic alcohols, surface active compositions are obtained having wetting properties which, while not exactly alike are comparable with those of the esters of sulpho-succinic acid, which are known to have outstanding properties in this respect. Thus the sodium salt of dioctylsulphosuccinate has a surface tension of about 30 d/cm. at a C.M.C. of a little less than 0.1%. Several of the new sulpho-esters according to the invention attains about the same value of surface tension, but at the very much lower concentration of about 0.001% to 0.01%. Sinking times according to the Draves test of some members are also comparable to that of the mentioned sulphosuccinate ester. Furthermore the new sulpho-esters of the wetting type offer certain advantages compared with known esters. They are transportable and storable in the form of more or less concentrated aqueous solutions, resulting in easy and ready use.

Detergents which are particularly useful as laundering agents, and which combine good wetting, emulsifying and detergent properties, are derived from a mixture of esters consisting of 65 to 85 mol.% of a $C_1$–$C_6$ alcohol (including mixtures thereof) and from 35 to 15 mol.% of a $C_{10}$–$C_{20}$ alcohol (including mixtures thereof). A specific and particular valuable example of the above type is a surface-active agent derived from butyl alcohol and myristyl alcohol. Other useful surface-active agents are derived from a mixture of one or more $C_1$–$C_6$ alcohols together with fatty alcohols, to give balanced hydro- and lipo-philic properties.

Particularly good anti-foam agents according to the invention are preferably obtained by esterification with $C_8$+ aliphatic monohydric alcohol or a mixture of aliphatic monohydric alcohols containing an average chain length of at least 8 carbons. To obtain optimum results in particular foam-producing media, such as detergent compositions, proteins, saponins, etc., of media of extreme conditions of pH or temperature, some modification of the alcohol components may be necessary to achieve optimum effect, the modification necessary being readily determinable.

Emulsifying agents according to the invention are obtainable by selecting the esterifying alcohols to obtain a predetermined hydrophilic/lipophilic ratio, according to known principles.

Degreasing agents according to the invention are obtainable for instance by esterifying about half of the carboxyl function with one or more $C_8$–$C_{12}$ alcohols, which may be branched or straight-chain alcohols, the rest of the carboxyl function being esterified with one or more lower alcohols.

The sulphonic acid residue of the surface-active agents of the invention may be associated with any salt-forming metal to form the sulphonic acid salt. Sodium and calcium sulphonate esters are the most useful. A surprising characteristic of the sodium sulphonate esters, is that they are soluble in hydrocarbon, particularly petroleum fractions.

The use of branched-chain alcohols to form the surface-active agents of the invention is in no way an obstacle for biodegradation notwithstanding the generally accepted theory that branching retards or stops biodegradation. It has been found that the complete biodegradation of the surfactive compositions according to the invention proceeds rapidly, the microbiological flora not being disturbed by the presence of the new surface-active substances according to the invention. It is possible that the good biodegradability of the new surfactants is due to the absence of an aromatic nucleous. Only in instances where the surface-active agents are derived wholly from $C_1$–$C_5$ alcohols that are branched e.g. isobutyl alcohol, is the biodegradation hampered to some extent. Surfactants derived from the new sulpho-acids and long chain alcohols e.g. $C_6$–$C_{21}$ alcohols, are biodegradable, notwithstanding that the alcohols are branched chain alcohols. If the surfactant according to the invention is derived from a mixture of such long chain alcohols and short chain alcohols, the surfactant material is biodegradable notwithstanding that the short chain alcohols are branched.

Thus for the preparation of the new surface-active compositions, branched-chain alcohols may be used, as well as long chain and short chain alcohols, the said branched alcohols hitherto finding limited acceptability because of the problem of biodegradability.

The toxicity of the new compounds is low. It has also been found, for instance, that fermentation on industrial scale by means of yeasts, moulds and bacteria are not disturbed by the new compounds when used, for instance, as anti-foaming agents and in fact were generally improved by their use.

Examples of the preparation of surface active agents according to the invention are provided by the following Examples 9 to 11.

EXAMPLE 9

A 40% aqueous solution of sodium bisulphite were progressively added over a period of 4 hours, to 67 kg of the ester mixture obtained as described in Example 5. A total amount of 15.3 kg of sodium bisulphite was used. At the same time, about 40 l. of ethyl alcohol were also progressively introduced into the reaction vessel under constant agitation, the temperature being held at 75° C. Thereafter the vessel was closed and the temperature raised from 100° to 105° C and the reaction continued for 12 more hours at a maximum pressure of 2 kg/cm2. After evacuating the alcohol by distillation, a reddish solution was obtained containing sodium salts of sulphonated pentyl esters.

By evaporation of water under reduced pressure, a homogeneous concentrated solution of the new product was obtained. This mixture of sulpho ester sodium salts was highly surfactive and showed excellent wetting agents combined with good emulsifying power, and was able to incorporate a substantial amount of water in organic solvents such as perchloroethylene and Stoddard solvent, used in dry-cleaning.

EXAMPLE 10

50 l. of the concentrated sulpho-acid solution obtained as described in Example 7, 25.4 kg 2-ethylhexanol and 24.3 kg 1-pentanol were introduced into a reaction vessel provided with an agitator.

The reaction was carried out at a temperature between 60° and 90° C at a reduced pressure of 60 to 200 mm Hg. An azeotropic mixture, mainly consisting of 1-pentanol and water, was distilled off and collected in a water separator, the supernatant alcoholic layer being continuously returned to the reaction vessel. After 5 hours the degree of esterification was 97%. The reaction mixture was neutralised to pH 7.0 by adding 14.7 l. of an 8 molar solution of sodium hydroxide. Excess of alcohol was removed by distillation under reduced pressure. By evaporation of water under reduced pressure, first a homogeneous concentrated solution and later a waxy solid product was obtained. The new product thus obtained was easily dispersed in water and showed excellent wetting properties combined with high dispersion power.

The new product (unpurified) was tested according to the Draves Clarkson procedure (using distilled water) modified in that a canvas disc was used instead of a cotton skein. The results, compared with a sodium dioctyl sulpho-succinate control, were as follows:

| product | concentration | sinking time (average of 6 measurements) |
|---|---|---|
| sodium dioctyl sulpho-succinate (analytical grade) | 0.01 % | 1' 09" |
| new product | 0.01 % | 1' 14" |

EXAMPLE 11

50 l. of the concentrated sulpho-acid solution obtained as described in Example 7, 20.9 kg 1-tetradecanol and 35.0 kg butyl alcohol were introduced into a reaction vessel. The reaction was carried out as described in Example 10, the azeotropic mixture mainly consisting of butyl alcohol and water. After 8 hours the degree of esterification was 98%. The reaction mixture was neutralised and excess of alcohol and water removed as described in Example 10. A yellow solid product was finally obtained which was highly surfactive. The surface tension of a 0.1% aqueous solution, measured with a Du Nouy tensiometer, was 24 dynes/cm.

The new product showed excellent detergent properties as will appear from the following comparative test in which test swatches of standard coiled cotton was washed in a "Launder-0-Meter" standard washing machine for 20 minutes at a temperature of 85° C using dodecylbenzene sulphonate as a control.

| product | concentration in distilled water | percent dirt removal |
| --- | --- | --- |
| dodecylbenzene sulphonate | 1 g /liter | 46.0 % |
| new product | 1 g /liter | 62.9 % |

Practical tests in home and industrial washing machines confirm the high detergency power of the new products in the absence as well as the presence of builders. Further, the new products can be used with or without builders in the preparation of concentrated solutions, so that they are especially suitable as general liquid detergents, and as detergents for special applications requiring a high degreasing power, such as in dish washing.

An example of an anti-foaming agent according to the invention is hereinafter provided.

EXAMPLE 12

50 l. of the concentrated sulpho-acid solution obtained as described in Example 7, 23.6 kg cetyl alcohol and 53.4 kg 2-ethylhexanol were introduced into a reaction vessel. The reaction was carried out as described in Example 10, the azeotropic mixture consisting mainly of 2-ethyl hexanol and water. After 6 hours the degree of esterification was 98%. The reaction mixture was neutralised and excess of alcohol and water removed as described in Example 10. A homogeneous syrupy concentrated solution was first obtained, and finally a yellowish solid product was obtained.

The new product could easily be dispersed in water and formed emulsions that were easy to use. The new product showed outstanding anti-foaming properties and was able to kill foams which were resistant to the usual commercial anti-foaming agents.

Anti-foam compositions of very high efficiency can be obtained by dissolving the sulpho-ester materials in organic solvents, for instance hydrocarbons. However, anti-foamant sulpho-esters which are effective in aqueous systems do not necessarily show the same efficiency in breaking foam in a non-aqueous system. Further, a solution of a relatively more hydrophilic anti-foamant in an organic solvent, e.g. gas oil, may be equally effective in aqueous systems compared with a relatively less hydrophilic anti-foamant.

This somewhat unusual behaviour is possibly due to the high solubility of the sulpho-esters of the invention in solvents such as petroleum distillates. To illustrate this point, the following data is provided.

Two known surface-active agents and the surface-active agent produced according to Example 10, were admixed with 80°–100° C petroleum ether. The solubilities were as follows:

| Surface-active Agent | Solubility Petroleum Ether g/liter |
| --- | --- |
| Sodium Lauryl Sulphate | 0.68 |
| Sodium Dodecylbenzenesulphonate | 0.23 |
| Surface-active material of Example 10 | Completely Soluble |

The solubility of the metal-containing surface-active agents according to the invention in hydrocarbons, including light and heavy petroleum distillates, combined with their pronounced dispersant and detergent properties and their ability to solubilize or fix aqueous components, makes them particularly suitable as additives for petroleum fuel or lubricating oils, and also in dry cleaning solvents such as chloroethylenes and "Stoddart" white spirit.

The surface-active agents of the invention may be prepared in powder-form, for use either alone or in combination with builders and/or fillers. It has been found that when the surface-active agents, for instance in powder form, are used in combination with other detergents, for instance synthetic detergents such as benzene dodecyl sulphate or dodecyl benzene sulphonate, or lauryl sulphate, said other detergents are in many instances upgraded in their action. When used with soaps, e.g. fatty salts of fatty acids, the surface-active agents of the invention inhibit or prevent the formation of insoluble calcium salts when used in hard water.

Commercially-useful compositions are provided by compositions comprising a surface-active agent according to the invention, with a liquid carrier, to form gels, solutions, or disperse compositions such as emulsions, pastes and creams. The said liquid carrier may be an aqueous medium, or an organic medium, for instance a liquid hydrocarbon, such as highly refined narrow out light petroleum fractions used in toilet and medical preparations.

By way of example, the following broad formulation of detergent composition is provided, which may be adapted for use in a wide range of applications, including domestic and industrial uses.

| | |
| --- | --- |
| Sulpho-ester according to the invention | 10–15 % by weight |
| Sodium carboxymethyl cellulose | about 0–5 % by weight |
| Sodium tripolyphosphate | 0–40 % by weight |
| Sodium perborate | 0–30 % by weight |
| Soda ash | 0–50 % by weight |
| Sodium pyrophosphate | 0–20 % by weight |
| Sodium metasilicate | 0–20 % by weight |
| Sodium sulphate | balance. |

It is to be understood that the above general formulation is not limiting, and that other conventional fillers and/or builders may be provided, including for example other sulphonated or sulphated surfactive components hitherto known and used in comparable formulations.

The formulations may be in the form of an aqueous solution.

The new acid and sulpho-acid materials can also be used in the preparation of amide or ester-amide materials. For this purpose the acid and sulpho-acid materials of the invention can be reacted with compounds containing basic amino groups such as lower and higher amines, and amino alcohols such as mono-, di- and tri-ethanolamine. It is to be noted that if amino alcohols are used, the amino as well as the hydroxyl groups may undergo a condensation reaction with the carboxylic acid group present in the acids or sulpho-acid material, so that the results of the reaction will depend mainly upon the reaction conditions. Further, if such compounds with basic amino groups are used, the esterification and/or amidification of all or any of the carboxyl groups and the neutralisation of the sulphonic acid groups on the same molecule, can be effected.

If one or more polyhydric alcohols, or a mixture of polyhydric alcohol(s) and monohydric alcohol(s), are used as esterifying agents for the sulphonated acid materials according to the invention, to produce partial esters thereof, polycondensates are produced which possess ion-exchange properties, due to the sulphonic acid groups and free carboxyl groups present in the resin. An example of such an ion-exchange resin is hereinafter provided.

EXAMPLE 13

2.500 milliequivalents of the sulpho-acid material obtained as described in Example 7, were reacted with 49 g of glycerol in a breaker provided with a stirrer. The temperature was gradually raised over 3 hours to 160° C by means of a heated oil bath. A jelly like product is obtained that solidified on cooling.

The new product showed a high absorption power with respect to cations, so that it could be used as ion-exchanger.

If one or more polyhydric alcohols, or a mixture of polyhydric alcohol(s) and monohydric alcohol(s), are used as esterifying agents for the acid materials according to the invention, plastics materials are obtainable. An example of such a material is hereinafter provided.

EXAMPLE 14

5.000 milliequivalents of the acid material obtained as described in Example 3 and 292 g of diethylene glycol, were introduced into a four-necked flask equipped with a stirrer and a nitrogen inlet. The temperature was gradually raised to 150° C over a period of three hours, and nitrogen was passed through the flask. After distillation of the water present in the reaction mixture, the remaining diethylene glycol was distilled under a reduced pressure of 10 to 20 mm Hg. An orange rubberlike polycondensate, insoluble in water and in most of the usual organic solvents, was obtained.

What is claimed is:

1. A method of preparing sulphonated salt material, which comprises (a) heating an alkaline-earth metal salt of citric acid to a temperature in the range of 230° C. to 400° C. for a period of time until an increase in titratable alkalinity of the reaction mixture is obtained, whereby an unsaturated organic salt material is obtained, (b) forming an aqueous solution or dispersion of the unsaturated organic salt material and (c) contacting said solution or dispersion with a bisulphite ion under acid conditions.

2. A method as claimed in claim 1, in which a bisulphite or sulphite compound is added to the solution or dispersion of the unsaturated organic salt material as the source of bisulphite ions.

3. A method as claimed in claim 1, in which $SO_2$ is injected into the solution or dispersion of the unsaturated organic salt material, whereby bisulphite ions are formed in situ in said solution.

4. A sulphonated salt material prepared by the method claimed in claim 1.

5. A method of preparing sulphonated organic acid material, which comprises (a) heating an alkaline-earth metal salt of citric acid to a temperature in the range of 230° C. to 400° C. for a period of time until an increase in titratable alkalinity of the reaction mixture is obtained, whereby an unsaturated organic salt material is obtained, (b) forming an aqueous solution or dispersion of the unsaturated organic salt material, (c) contacting said solution or dispersion with a bisulphite ion under acid conditions whereby a sulphonated salt material is obtained and (d) hydrolyzing the sulphonated salt material.

6. A method of preparing sulphonated organic acid material, which comprises (a) heating an alkaline-earth metal salt of citric acid to a temperature in the range of 230° C. to 400° C. for a period of time until an increase in titratable alkalinity is obtained, whereby an unsaturated organic salt material is obtained, (b) acidifying an aqueous solution or dispersion of the unsaturated organic salt material to a pH of 7 or less, (c) injecting $SO_2$ in the solution or dispersion thus obtained to form sulphonated organic salt material, (d) contacting the sulphonated organic salt material with an acid whereby the sulphonated organic salt material is hydrolyzed and (e) recovering a solution of free sulphonated organic acid material.

7. A method as claimed in claim 6, in which the acid used in step (b) is a portion of the product solution from step (e) of free sulphonated organic acid material.

8. Sulphonated acid material prepared by the method claimed in claim 7.

9. A method of preparing sulphonated organic acid material, which comprises (a) heating an alkaline-earth metal salt of citric acid to a temperature in the range of 230° C. to 400° C. for a period of time until an increase in titratable alkalinity is obtained, (b) hydrolyzing the reaction product thus obtained to form corresponding organic acid material, (c) forming an aqueous solution or dispersion of the acid material and (d) contacting said solution or dispersion with bisulphite ions.

10. A method as claimed in claim 9, in which a bisulphite or sulphite compound is added to the solution or dispersion of the acid material as the source of bisulphite ions.

11. A method as claimed in claim 9, in which $SO_2$ is injected into the solution or dispersion of the acid material, whereby bisulphite ions are formed in situ in said solution.

* * * * *